United States Patent [19]

Dunbar

[11] 4,380,649

[45] Apr. 19, 1983

[54] ISOPHORONE DERIVATIVES

[75] Inventor: Joseph E. Dunbar, Midland, Mich.

[73] Assignee: The Dow Chemical Company, Midland, Mich.

[21] Appl. No.: 324,193

[22] Filed: Nov. 23, 1981

[51] Int. Cl.$^3$ .................. C07D 309/38; C07D 311/18
[52] U.S. Cl. .................................... 549/285; 549/292; 568/367; 424/279; 424/281; 424/331
[58] Field of Search .................. 260/343.44; 549/285, 549/292; 568/367

[56] References Cited

U.S. PATENT DOCUMENTS

| | | | |
|---|---|---|---|
| 2,427,578 | 9/1947 | Stahman et al. | 549/285 |
| 3,810,922 | 5/1974 | Dunbar | 549/285 |
| 3,957,824 | 5/1976 | Hadler et al. | 549/285 |
| 3,974,289 | 8/1976 | Buckle et al. | 549/285 |

Primary Examiner—Jane T. Fan
Attorney, Agent, or Firm—John M. Sanders

[57] ABSTRACT

Novel isophorone derivatives are disclosed and possess utility as insect sterilants, plant growth regulators and fungicides.

7 Claims, No Drawings

ISOPHORONE DERIVATIVES

SUMMARY OF INVENTION

The present invention is directed to novel isophorone derivatives corresponding to the formula

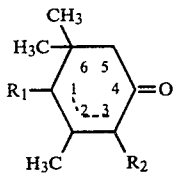
(I)

wherein the dotted line represents a double bond in the 1-2 or the 2-3 ring position, when $R_1$ represents

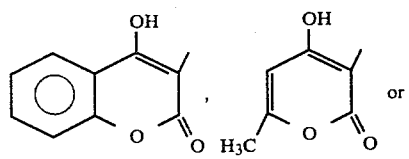
(II)

then $R_2$ represents hydrogen and the double bond is in the 1-2 ring position; otherwise $R_1$ represents hydrogen, and $R_2$ represents

(III)

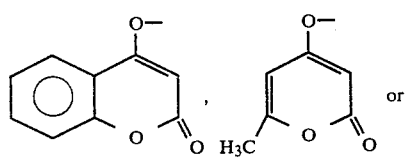

and the double bond is in the 2-3 ring position.

The present compounds are useful as insect sterilants, plant growth regulators and fungicides.

Detailed Description of the Invention

The compounds of the present invention are crystalline solids at ambient room temperature which are of low solubility in water and slightly soluble in common organic solvents such as methylene chloride.

The new compounds of the present invention are prepared by reacting a 4-haloisophorone compound with an appropriate 4-hydroxycoumarin compound, an appropriate cyclohexenone compound or an appropriate pyranone compound. This reaction takes the form of an O-alkylation and a C-alkylation reaction.

The O-alkylation reaction involves the attachment of the isophorone starting material to the hydroxy oxygen atom in the second starting material, i.e., the 4-hydroxycoumarin compound, the cyclohexenone compound or the pyranone compound. This O-alkylation reaction can be characterized as follows:

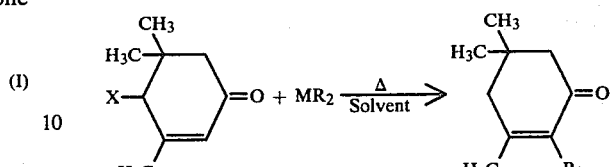

wherein

X represents chloro, bromo, or iodo;

$MR_2$ represents an alkali metal salt of 4-hydroxycoumarin, 5,5-dimethylcyclohexane-1,3-dione or 4-hydroxy-6-methyl-2H-pyran-2-one, and $R_2$ is as hereinbefore defined.

The C-alkylation reaction involves the attachment of the isophorone starting material to a ring carbon atom of the second starting material, i.e., the 4-hydroxycoumarin, the cyclohexenone or the pyranone compound. The C-alkylation reaction can be characterized as follows:

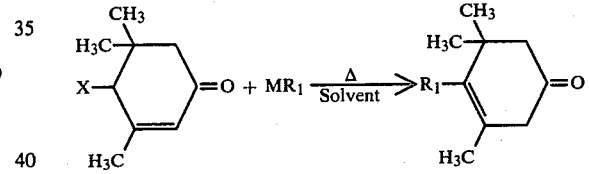

wherein

X and $R_1$ are as hereinbefore defined, and $MR_1$ represents an alkali metal salt of 4-hydroxycoumarin, 5,5-dimethylcyclohexane-1,3-dione or 4-hydroxy-6-methyl-2H-pyran-2-one.

The O-alkylation and C-alkylation described above take place simultaneoulsy when the starting materials described herein are reacted. To illustrate this, the reaction of 4-bromoisophorone and the sodium salt of 5,5-dimethylcyclohexane-1,3-dione is characterized as follows:

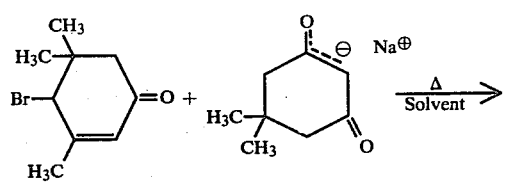

-continued

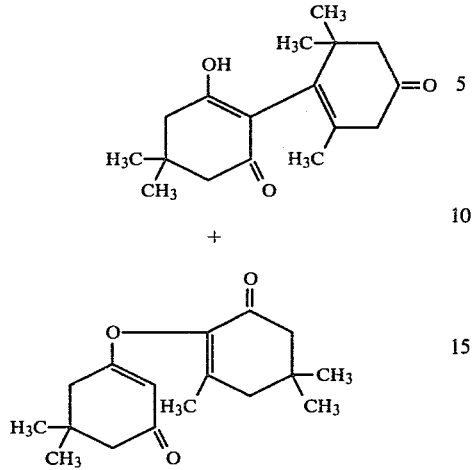

+

No attempt has been made to balance the above equation.

In carrying out the above reactions, the 4-haloisophorone and the appropriate hydroxycoumarin, cyclohexenone or pyranone compound are dissolved in a solvent such as, for example, dimethylformamide (DMF), a preferred solvent, or ethanol. The reactants are advantageously maintained under agitation during the reaction period. The reaction is carried out at temperatures between about 25° C. and about 125° C., and preferably between about 80° and 100° C. Depending upon the specific reactants and solvent employed, the reaction is usually complete in from about 1 to about 36 hours. Upon completion of the reaction, the reaction mixture is poured into cold water or poured over ice and the crude solid product which precipitates is recovered by filtration or other conventional separatory procedures. The product can then be purified by employing conventional purification techniques.

The molar proportion of reactants employed in making the present compounds is not critical but can range from equimolar proportions up to a threefold molar excess of the 4-haloisophorone reactant.

Compounds having an —OH group on the coumarin, cyclohexenone and pyranone moiety, i.e., when $R_1$ is not hydrogen (see Formula II), will exist in a tautomeric equilibrium with a corresponding keto compound. For example, the following compound exists in a tautomeric equilibrium between the enol and the keto forms

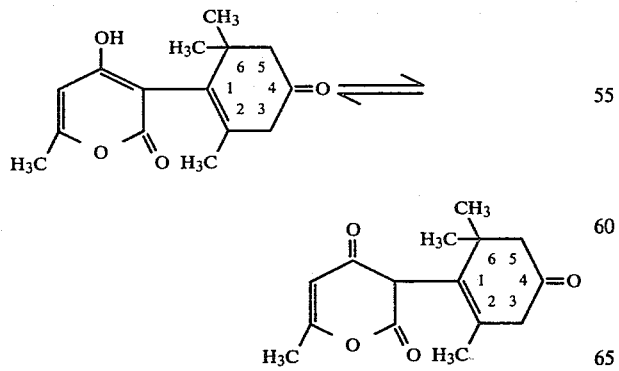

It is contemplated by the present invention to include both tautomeric forms when such exist.

The following examples illustrate the present invention and the manner by which it can be practiced but, as such, should not be construed as limitations upon the overall scope of the same.

EXAMPLE 1

3-Hydroxy-5,5-dimethyl-2-(2,6,6-trimethyl-4-oxo-1-cyclohexen-1-yl)-2-cyclohexen-1-one monohydrate

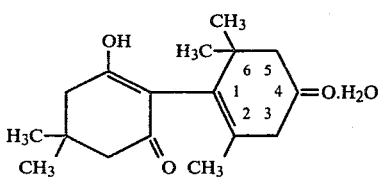

A mixture of 16.3 grams (g) (0.0750 mole) of 4-bromoisophorone, 10.5 g (0.0750 mole) of 5,5-dimethylcyclohexane-1,3-dione, 2 milliliters (ml) of dimethylformamide (employed as a catalyst) and 3.0 g (0.075 mole) of sodium hydroxide in 200 ml of ethanol was heated under reflux with stirring for 25 hours. At the end of this period some starting material was shown still to be present by thin layer chromatographic analysis. The ethanol was removed by evaporation, in vacuo, and the resulting residue dissolved in 100 ml of DMF. The reaction mixture was then heated on a steam plate at between 85° C. and 95° C. for three hours after which the mixture was then cooled and poured into 800 ml of ice water, precipitating the crude product as a light yellow solid, which was air dried and washed with ethyl ether to give the pure 3-hydroxy-5,5-dimethyl-2-(2,6,6-trimethyl-4-oxo-1-cyclohexen-1-yl)-2-cyclohexen-1-one monohydrate as a cream colored solid which had a melting point of 132°–134° C. Upon analysis, the product was found to have carbon and hydrogen contents of 69.4 and 8.84 percent, respectively, as compared with the theoretical contents of 69.36 and 8.90 percent, respectively, calculated for $C_{17}H_{26}O_4$. The structure of the product was confirmed by its nuclear magnetic resonance spectrum.

EXAMPLE 2

6-Methyl-4-[(2,4,4-trimethyl-6-oxo-1-cyclohexen-1-yl)oxy]-2H-pyran-2-one

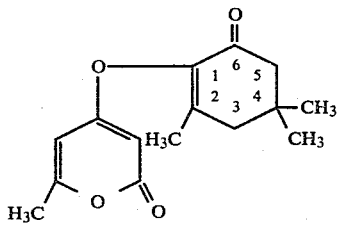

A mixture of 15.0 g (0.0691 mole) of 4-bromoisophorone and 10.2 g (0.0691 mole) of the sodium salt of 4-hydroxy-6-methyl-2H-pyran-2-one in 100 ml of DMF was heated on a steam plate between 85° C. and 95° C. for three hours after which the mixture was cooled and poured into 750 ml of ice water, precipitating the crude product as a brown, gummy precipitate. This precipitate was extracted with ether and then the extract was washed with three 200 ml portions of water and dried over anhydrous sodium sulfate. The sodium sulfate was removed by filtration and the ether was thereafter removed by evaporation in vacuo, leaving a viscous, amber oil. This oil was then dissolved in 150 ml of methylene chloride and the solution was washed with four 50 ml portions of 5% aqueous sodium hydroxide and one 50 ml portion of water. The methylene chloride solution was then dried over anhydrous sodium sulfate and evaporated leaving the product as a brown oil. The oil was crystallized by trituration with ethyl ether to give the pure 6-methyl-4-[(2,4,4,-trimethyl-6-oxo-1-cyclohexen-1-yl)oxy]-2H-pyran-2-one as a light tan, crystalline solid, which had a melting point of 119.5°–121° C. Upon analysis, the product was found to have carbon and hydrogen contents of 68.8 and 6.93 percent, respectively, as compared with the theoretical contents of 68.68 and 6.92 percent, respectively, calculated for $C_{15}H_{18}O_4$. The structure of the product was confirmed by its nuclear magnetic resonance spectrum.

EXAMPLE 3

4-Hydroxy-3-(2,6,6-trimethyl-4-oxo-1-cyclohexen-1-yl)coumarin and
4[(2,4,4-trimethyl-6-oxo-1-cyclohexen-1-yl)oxy]coumarin

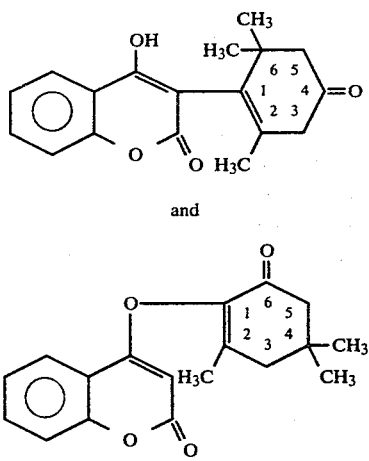

A mixture of 42.0 g (0.194 mole) of 4-bromoisophorone and 34.0 g (0.185 mole) of the sodium salt of 4-hydroxycoumarin in 300 ml of DMF was heated between 90° C. and 95° C. for 2 hours after which the mixture was cooled and poured into 1500 ml of ice water, whereby a gummy precipitate formed which was extracted with ethyl ether. A cream colored solid (6.3 g), having a melting point of 156°–158° C., crystallized from the wet ether extract and, upon analysis, was confirmed as being 4-[(2,4,4-trimethyl-6-oxo-1-cyclohexen-1-yl)oxy]coumarin hereinafter referred to as Batch A.

The remaining ether extract was dried over anhydrous sodium sulfate and the ether was removed by evaporation. The residue was dissolved in methylene chloride, and this solution was then extracted with two 200 ml portions of 5% aqueous sodium hydroxide solution. The organic phase, hereinafter referred to as ("B"), was set aside while the aqueous phase was treated with activated charcoal, filtered and then acidified with dilute hydrochloric acid to give a gummy, semi-solid. The semi-solid was extracted with methylene chloride, and then the extract was dried over anhydrous sodium sulfate and anhydrous magnesium sulfate together, filtered and evaporated to dryness. The residue, thus formed, was crystallized from aqueous ethanol to give 4-hydroxy-3-(2,6,6-trimethyl-4-oxo-1-cyclohexen-1-yl)coumarin as a white, crystalline solid, having a melting point of 195° C. Upon analysis, the product was found to have carbon and hydrogen contents of 72.23 and 6.01 percent, respectively, as compared with the theoretical contents of 72.46 and 6.08 percent, respectively, calculated for $C_{18}H_{18}O_4$. The structure of the product was confirmed by its infrared and nuclear magnetic resonance spectra.

The organic phase "B" was washed with water and dried over anhydrous sodium sulfate. The methylene chloride was removed by evaporation, and the resulting residue was crystallized from carbon tetrachloride to give 4-[(2,4,4-trimethyl-6-oxo-1-cyclohexen-1-yl)oxy]coumarin, having a melting point of 157°–158° C., and was combined with batch A. Upon analysis, the product was found to have carbon and hydrogen contents of 72.18 and 6.27 percent, respectively, as compared with the theoretical contents of 72.46 and 6.08 percent, respectively, calculated for $C_{18}H_{18}O_4$. The structure of the product was confirmed by its infrared and nuclear magnetic resonance spectra.

The compounds of the present invention are useful as insect sterilants, plant growth regulators and fungicides. This is not meant to suggest that all of the compounds are equally effective against the same insects, plants or organisms or at the same concentrations.

For use as insect sterilants the present compounds are administered to insects in an amount effective to decrease the number of eggs produced by the insects and also to decrease the number of viable eggs which are produced by such insects. Insects in which this sterilizing effect is desirable include ants, flies, aphids, katydids, cicadae, locusts, mosquitos and grasshoppers. The present compounds are administered to said insects by contacting the insects, their habitat or their food supply with a compound of the present invention or a mixture of such compounds whereby the desired effect is achieved. The compounds of the present invention may also be applied directly to eggs whereby a decrease in viability of the treated eggs is achieved. Generally, an insect sterilizing amount is accomplished by providing a composition containing from about 0.1 to about 1000 parts per million by weight (ppm) of active ingredient to be administered as described above. The optimum dose of active ingredient will vary depending on the insect involved and the particular active ingredient employed and is readily determinable to one skilled in the art by the use of dose titration determinations.

In a representative operation for the control of plant-eating insects, the present compounds are applied to the plants, which are eaten by the insects to be controlled, in an amount sufficient to inhibit the reproducing capability of the insects. The present compounds are conveniently incorporated into a spray composition and sprayed onto the plants employing well known formulating and spraying procedures.

In a further representative operation for the control of non-plant-eating insects, such as, the housefly and the fruit fly, the present compounds are conveniently applied directly onto the insects or their habitat in an amount sufficient to inhibit the reproducing capability of the insects. Alternatively, insect eggs are directly contacted with compositions containing the present compounds in an amount to reduce the viability of such treated eggs. The present compounds are conveniently incorporated into sprays, aerosols, dusts, pellets or traps employing well-known formulation and application procedures.

The compounds of the present invention also exhibit antifungal properties. In a representative operation when 4-[(2,4,4-trimethyl-6-oxo-1-cyclohexen-1-yl)oxy]-coumarin, when employed as the sole toxicant in an aqueous composition at a concentration of 400 ppm of the ultimate composition, was found to give substantially complete kill and control of *Trichophyton mentagrophytes*.

The present compounds are also active as plant growth regulators. In a representative operation, when 4-hydroxy-3-(2,6,6-trimethyl-4-oxo-1-cyclohexen-1-yl)coumarin was applied at a rate of 10 lbs/acre preemergently to beans, soybeans, corn, cotton and wheat, the percent stunting of the aforementioned plants was 5.5, 78, 13, 19 and 47 percent, respectively, when compared to an untreated control.

In another representative operation, when 4-[(2,4,4-trimethyl-6-oxo-1-cyclohexen-1-yl)oxy]coumarin was applied at a rate of 20 lbs/acre preemergently to foxtail, crabgrass, beans, wild mustard, pigweed and bindweed, the percent stunting of the aforementioned plants was 50, 70, 50, 60, 80 and 50 percent, respectively, when compared to an untreated control.

For the uses described above, the compounds of the present invention or their mixtures can be employed in unmodified form or dispersed in a finely divided solid and employed as dusts. Such mixtures can also be dispersed in water with the aid of a surface-active agent and the resulting dispersions employed as sprays. In further procedures, the present compounds can be employed as active constituents in solvent solutions, oil-in-water or water-in-oil emulsions. When used as an insect sterilant it is advantageous to mix the present compounds with a substrate or diluent that will likely be ingested by the insects.

The compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of additional compounds(s).

STARTING MATERIALS

The starting materials employed herein are all known compounds. The 4-bromoisophorone is prepared by reacting the commercially available isophorone with a N-bromosuccinimide, also commercially available, employing procedures well known in the art. (See J. Chem. Soc. 1089 (1957).) 5,5-dimethylcyclohexane-1,3-dione, 4-hydroxy-6-methyl-2H-pyron-2-one, N-bromosuccinimide and 4-hydroxycoumarin are all commercially available compounds.

I claim:

1. A compound of the formula

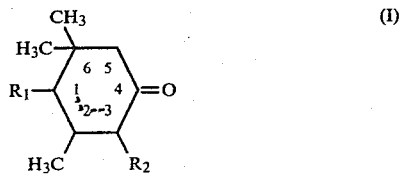

wherein
the dotted line represents a double bond in the 1–2 or the 2–3 ring position;
when $R_1$ represents

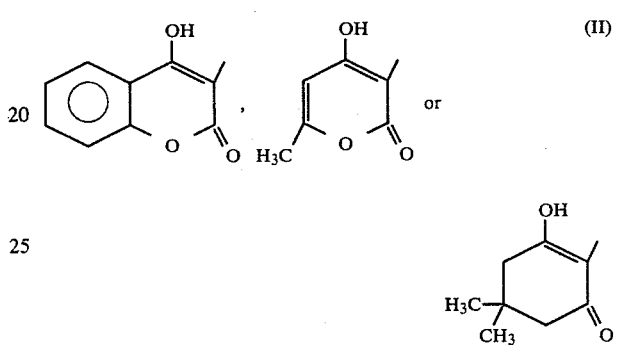

then $R_2$ is hydrogen and the double bond is in the 1–2 ring position; otherwise $R_1$ represents hydrogen, and
$R_2$ represents

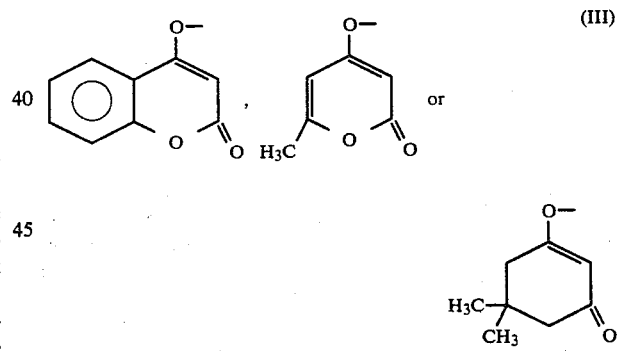

and the double bond is in the 2–3 ring position.

2. The compound of claim 1 which is 4-hydroxy-3-(2,6,6-trimethyl-4-oxo-1-cyclohexen-1-yl)coumarin corresponding to the formula

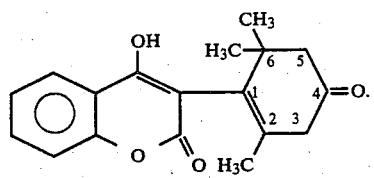

3. The compound of claim 1 which is 4-[(2,4,4-trimethyl-6-oxo-1-cyclohexen-1-yl)oxy]coumarin corresponding to the formula

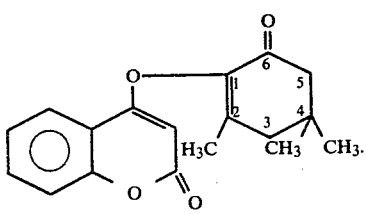

4. The compound of claim 1 which is 4-hydroxy-6-methyl-3-(2,6,6-trimethyl-4-oxo-1-cyclohexen-1-yl)-2H-pyran-2-one corresponding to the formula

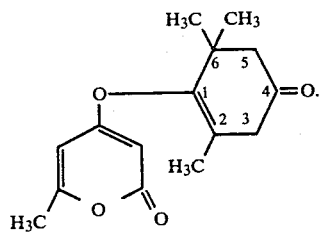

5. The compound of claim 1 which is 6-methyl-4-[(2,4,4-trimethyl-6-oxo-1-cyclohexen-1-yl)oxy]-2H-pyran-2-one corresponding to the formula

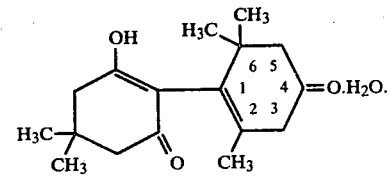

6. The compound of claim 1 which is 3-hydroxy-5,5-dimethyl-2-(2,6,6-trimethyl-4-oxo-1-cyclohexen-1-yl)-2-cyclohexen-1-one monohydrate corresponding to the formula

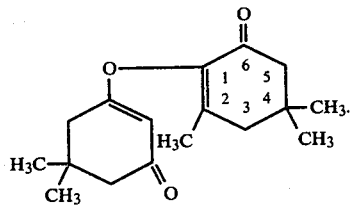

7. The compound of claim 1 which is 5,5-dimethyl-3-[(2,4,4-trimethyl-6-oxo-1-cyclohexen-1-yl)oxy]-2-cyclohexen-1-one corresponding to the formula

* * * * *

UNITED STATES PATENT AND TRADEMARK OFFICE
CERTIFICATE OF CORRECTION

PATENT NO. : 4,380,649
DATED : April 19, 1983
INVENTOR(S) : Joseph E. Dunbar

It is certified that error appears in the above—identified patent and that said Letters Patent is hereby corrected as shown below:

Col. 9, line 25 - Change formula to show:

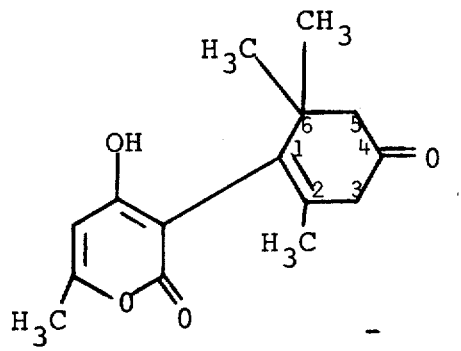

Col. 7, line 55 - "of additional compounds(s)." should read -- of the additional compounds(s). --.

Signed and Sealed this

Twenty-second Day of November 1983

[SEAL]

Attest:

GERALD J. MOSSINGHOFF

Attesting Officer    Commissioner of Patents and Trademarks